(12) United States Patent
Kobayashi et al.

(10) Patent No.: US 8,579,862 B2
(45) Date of Patent: Nov. 12, 2013

(54) APPLICATOR FOR MICRONEEDLE ARRAY (75) Inventors: Katsunori Kobayashi, Kagawa (JP); Hidetoshi Hamamoto, Kagawa (JP)

(73) Assignee: MEDRx Co., Ltd., Higashikagawa (JP)

( * ) Notice: Subject to any disclaimer, the term of this patent is extended or adjusted under 35 U.S.C. 154(b) by 0 days.

(21) Appl. No.: 13/202,931

(22) PCT Filed: Feb. 19, 2010

(86) PCT No.: PCT/JP2010/001102
§ 371 (c)(1),
(2), (4) Date: Oct. 20, 2011

(87) PCT Pub. No.: WO2010/095456
PCT Pub. Date: Aug. 26, 2010

(65) Prior Publication Data
US 2012/0029434 A1 Feb. 2, 2012

(30) Foreign Application Priority Data

Feb. 23, 2009 (JP) .................................. 2009-038788

(51) Int. Cl.
*A61M 5/00* (2006.01)
*A61F 13/00* (2006.01)

(52) U.S. Cl.
USPC ............................ 604/173; 604/115; 604/304

(58) Field of Classification Search
USPC ................. 604/304–307, 173–176, 115–117
See application file for complete search history.

(56) References Cited

U.S. PATENT DOCUMENTS

| 8,267,889 B2 * | 9/2012 | Cantor et al. ................. 604/115 |
| 2007/0005017 A1 | 1/2007 | Alchas et al. |
| 2008/0114298 A1 | 5/2008 | Cantor et al. |

FOREIGN PATENT DOCUMENTS

| EP | 2 127 693 A1 | 12/2009 |
| GB | 2 428 197 A | 1/2007 |
| JP | 2005-087519 A | 4/2005 |
| JP | 2006-149818 A | 6/2006 |
| JP | 2008-520369 A | 6/2008 |
| JP | 2008-543527 A | 12/2008 |
| WO | WO 2006/055795 A1 | 5/2006 |
| WO | WO 2007/002521 A2 | 1/2007 |
| WO | WO 2008/069566 A1 | 6/2008 |
| WO | WO 2008/091602 A2 | 7/2008 |
| WO | WO 2008/093679 A1 | 8/2008 |

OTHER PUBLICATIONS

Japanese Patent Office, International Search Report in International Patent Application No. PCT/JP2010/001102 (Mar. 23, 2010).
European Patent Office, Office Action in European Patent Application No. 10 743 585.1 (May 6, 2013).

* cited by examiner

*Primary Examiner* — Nicholas Lucchesi
*Assistant Examiner* — Rebecca E Eisenberg
(74) *Attorney, Agent, or Firm* — Leydig, Voit & Mayer, Ltd.

(57) ABSTRACT

Provided is a microneedle device which protects microneedle, has an easily portable shape, is free from such problems as breakage of small needles in the step of puncturing the skin with the microneedle, and ensures appropriate skin puncture for administering a drug. By studying the relationship between a device to be pressed to the skin and the height of an elevation on the skin surface under the pressing and thus producing a device equipped with microneedle that are embedded in a concave part having a definite depth, the microneedle can be surely and easily inserted and punctured into the skin while avoiding such problems as breakage of the small needles of the microneedle. Thus, a microneedle patch formulation, which is easily portable and ensures convenient drug administration to the skin, can be produced.

15 Claims, 13 Drawing Sheets

APPLICATOR FOR MICRONEEDLE ARRAY

TECHNICAL FIELD

The present invention relates to an applicator used to puncture skin with a pin-frog-shaped (*kenzan*-shaped) microneedle effectively. Also, the present invention relates to a method for plastering a patch formulation using the pin-frog-shaped microneedle.

BACKGROUND ART

Transdermal administration of drugs has been normally achieved by using formulations for transdermal administration in the form of solutions or ointments to be applied or plastered to the skin surface. The skin, in the case of human, normally comprises a number of tissues: the stratum corneum (horny layer) having a laminar structure in a thickness of 10 to 30 μm, the epidermal tissue layer in a thickness of about 70 μm, and the dermal tissue layer in a thickness of about 2 mm.

The stratum corneum, which is a laminar structure constituting the outermost layer of the skin, functions as a barrier to prevent various drugs from penetrating the skin. Generally, about 50 to 90% of the barrier action of the skin is attributed to the stratum corneum. The epidermal layer does not contribute to the barrier action as great as the stratum corneum; however it accounts for the remaining about 10% or more of the skin barrier action. Meanwhile, the dermal layer has an extensive capillary network in the vicinity of the junction between the dermal layer and the epidermal layer. Once a drug reaches the depth of the dermis, the drug quickly diffuses into deeper tissues (hair follicles, muscles and the like) through the capillary network. Then, the drug is systematically diffused through the blood circulation from the capillaries.

Currently, there have been developed various formulations for transdermal administration in the form of solutions or ointments to be applied or plastered to the skin surface. However, due to the barrier action of the stratum corneum described above, absorption of drug-effective components is insufficient. For example, it is said that, even formulations for transdermal administration of indomethacin, which are considered to exhibit high transdermal absorption rate, enable only about 5% of the total amount of indomethacin to be absorbed transdermally.

Accordingly, as one method to increase the skin permeability of a drug, as shown in Patent Document 1, it has been tried to topically destroy the stratum corneum using small needles (microneedle or microsyringe) to forcibly deliver the drug into the dermal layer.

The small needles used for this purpose have preferably 30 μm or more in length in order that they reach the dermal layer, and the small needles are considered to require a base for supporting the needles. Since the small needles do not reach the dermal layer where nerve terminals are located, they do not cause pain. Therefore, there is an advantage of administering a drug without causing fear to children, etc.

While a wide variety of methods for producing the microneedle have been studied, there also have been studied devices (i.e., assistive tool) for puncturing skin with the microneedle effectively. These devices employ a method of using impact force of a spring or the like to puncture skin with the microneedle (Patent Documents 2 and 3).

These puncturing methods of the microneedle using impact force, however, may cause easy breakage of the small needles of the microneedle in the step of puncturing the skin and also cause excessive damage to the skin surface. Therefore, there is a demand for devices that cause less impact and can be punctured softly. Accordingly, an array device in the form of a syringe has been reported, in which a piston is inserted into a tube and pressed by hand to puncture the skin slowly (Patent Document 4).

Patent Document 1: JP-A-2006-149818
Patent Document 2: JP-A-2008-520369
Patent Document 3: JP-A-2008-543527
Patent Document 4: WO 2008/069566

DISCLOSURE OF THE INVENTION

Problems to be Solved by the Invention

The present invention provides an applicator (insertion tool) for a microneedle array, which is convenient and portable. In particular, the microneedle made of a biodegradable resin (small needle parts) is not sufficiently strong, and therefore in many cases, when they approach the skin at angles other than vertical, they may be broken at the time of contact with the skin surface and cannot be inserted into the skin or may be broken at the time of insertion and remain embedded in the skin. Thus, there is provided an applicator which enables the microneedle made of a biodegradable resin to be surely and easily inserted into skin.

Means for Solving the Problems

Figure 1:
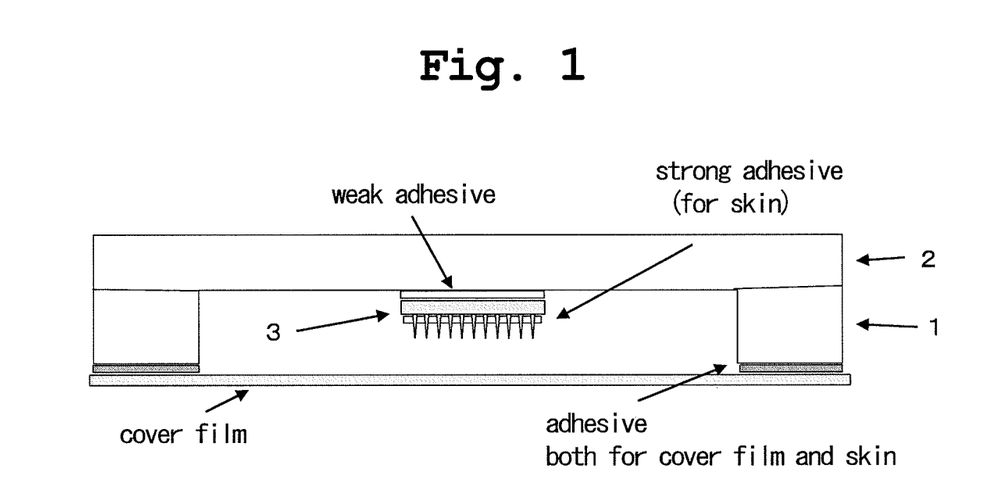
FIG. 1 is a cross-sectional view of a device of the present invention.

When the skin surface was pressed with a tubular hard member, it was seen that the skin inside the tubular member was slightly elevated and slightly entered into the tubular member. Observing the way the skin was elevated and protruded into the tubular member in detail, the following points became apparent. Here, a tubular member having a cut end perpendicular to the axis direction of the tubular member was used, and the cross-section thereof was pressed against the skin surface. At that time, the present inventors found out that, even when the pressing angle of the tubular member against the skin (an angle between the axis direction of the tubular member and the flat skin surface) was not a right angle, or even when the tubular member was shifted or moved slightly, this hardly affected the elevation on the skin surface inside the tubular member. Also, they found out that the direction of the elevation on the skin surface was approximately the same as the axis direction. Accordingly, the present inventors made a device having a concave part, in place of the tubular member, as shown in FIG. 1. In a bottom part of the concave member, a microneedle made of a biodegradable resin was placed. In regard to the tool having this shape, the present inventors studied a correlation between the shape of the concave part and the height of the elevation on the skin under the pressure of the tool, and thereby found out that there was a positive correlation between the distance of short side of the concave shape or the average of long side and short side thereof and the height of the elevation on the skin.

The present invention has been completed based on these findings and upon further studies, and a summary thereof is as follows.

(1) A microneedle device having a recessed shape, comprising:
 a fixing member for fixing a microneedle, and
 a supporting member at or near a periphery of the flat plate, wherein
 the microneedle is placed in a central part of the microneedle device such that:

a) tip portions of small needles of the microneedle are positioned inside the device from a tip surface of the supporting member; and
b) a distance between the tip portions of the small needles and the tip plane of the supporting member is "inner dimension (an average of long side and short side) of tip portion of the supporting member" ×15% or shorter.
(2) The microneedle device according to claim 1, wherein the inner dimension (an average of long side and short side) of the tip portion of the supporting member is 5 to 70 mm.
(3) The microneedle device according to claim 1 or 2, wherein the inner dimension (an average of long side and short side) of the tip portion of the supporting member is 5 to 50 mm.
(4) The microneedle device according to any of claims 1 to 3, wherein the shape of the recess at the tip portion of the supporting member is a circular shape, an elliptical shape, or a polygonal shape.
(5) The microneedle device according to claim 4, wherein the polygonal shape is a square shape.
(6) The microneedle device according to claim 4, wherein the circular shape has a diameter of 5 to 32 mm.

Effects of the Invention

Pressing the device of the present invention against the skin enables puncture of the skin, hardly causing breakage of the small needles, even though the microneedle is made of a biodegradable resin that has insufficient material strength. Further, since the device of the present invention is in the form of a small chip, it is easily portable, with the concave part being covered, and even ordinary people can remove the cover and administer a drug transdermally in a convenient manner.

EMBODIMENTS FOR CARRYING OUT THE INVENTION

Hereinafter, the present invention will be further explained in detail with reference to preferable aspects shown in the appended figures. In the figures, the same or corresponding components are indicated by the same numerals.

A microneedle device of the present invention is, for example, the one shown in FIG. 1. The device shown in FIG. 1 is a flat chip-shaped tool, in which a microneedle (3) is fixed to a fixing member (2). The microneedle is fixed to the fixing member (2) with a weak adhesive, and a cover film is fixed to a supporting member (1). The microneedle (3) is fixed such that the axis direction of small needles of the microneedle (3) is perpendicular to the fixing member (2). The cover film is used as a protection sheet in order to prevent the microneedle from being damaged. To use the chip-shaped tool of the present invention, first the cover sheet is detached therefrom, and then the chip-shaped tool is placed on the skin surface.

Figure 2:
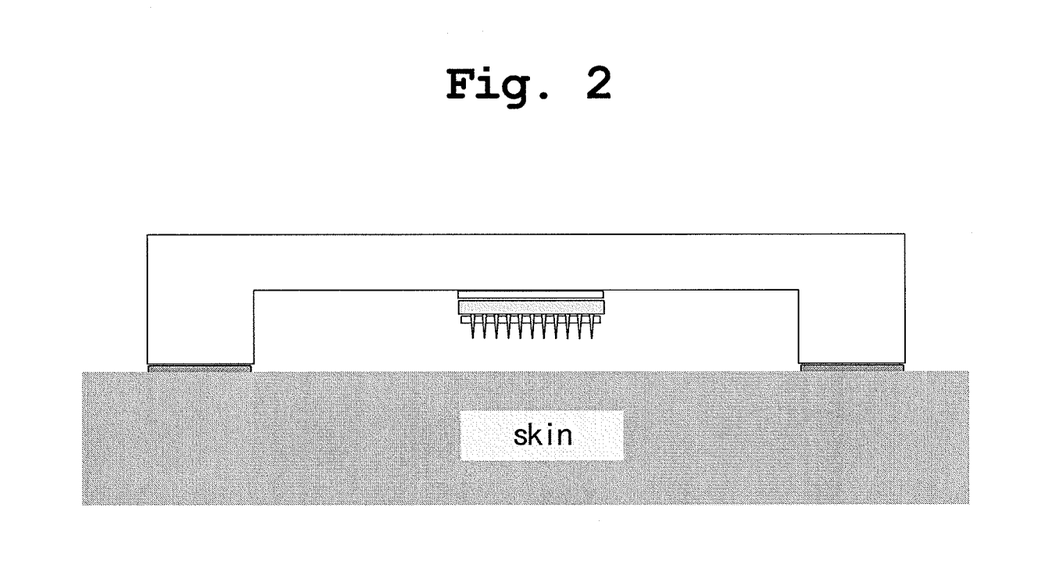
FIG. 2 is a cross-sectional view of the device of FIG. 1, in which a cover film of the device is detached therefrom and the device is placed on the skin surface.

As shown in FIG. 2, the adhesive for the cover film remaining in the supporting member (1) is firmly attached to the skin surface to fix the chip-shaped tool.

Figure 3:
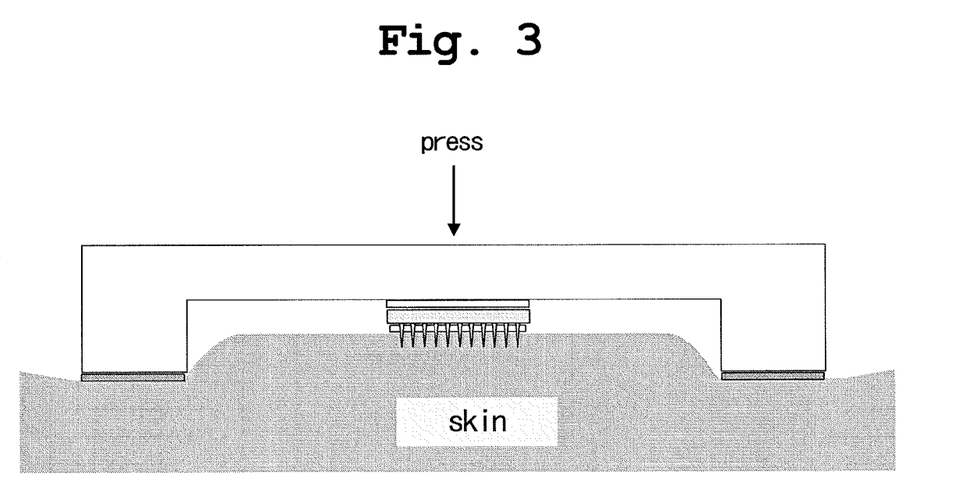
FIG. 3 is a cross-sectional view of the device of FIG. 1, showing that, when the device is pressed with a finger, the skin surface is elevated inside a concave part of the device, and the skin surface reaches an adhesive applied onto a base of the microneedle and is firmly attached thereto.
Figure 4:
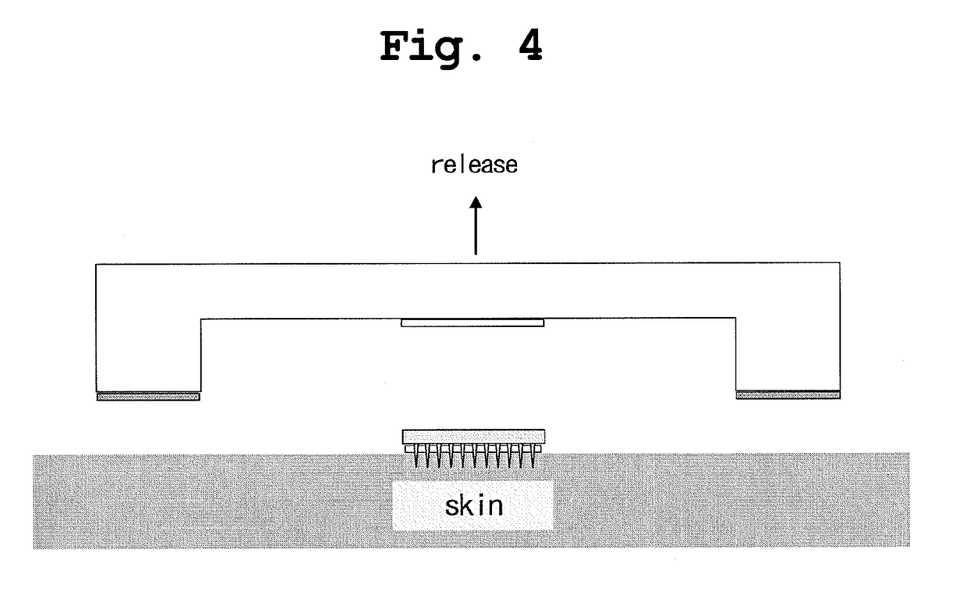
FIG. 4 is a cross-sectional view of the device of FIG. 1, showing that, when the pressure to the device is released to remove the device, the microneedle is detached from the device.
Figure 17:
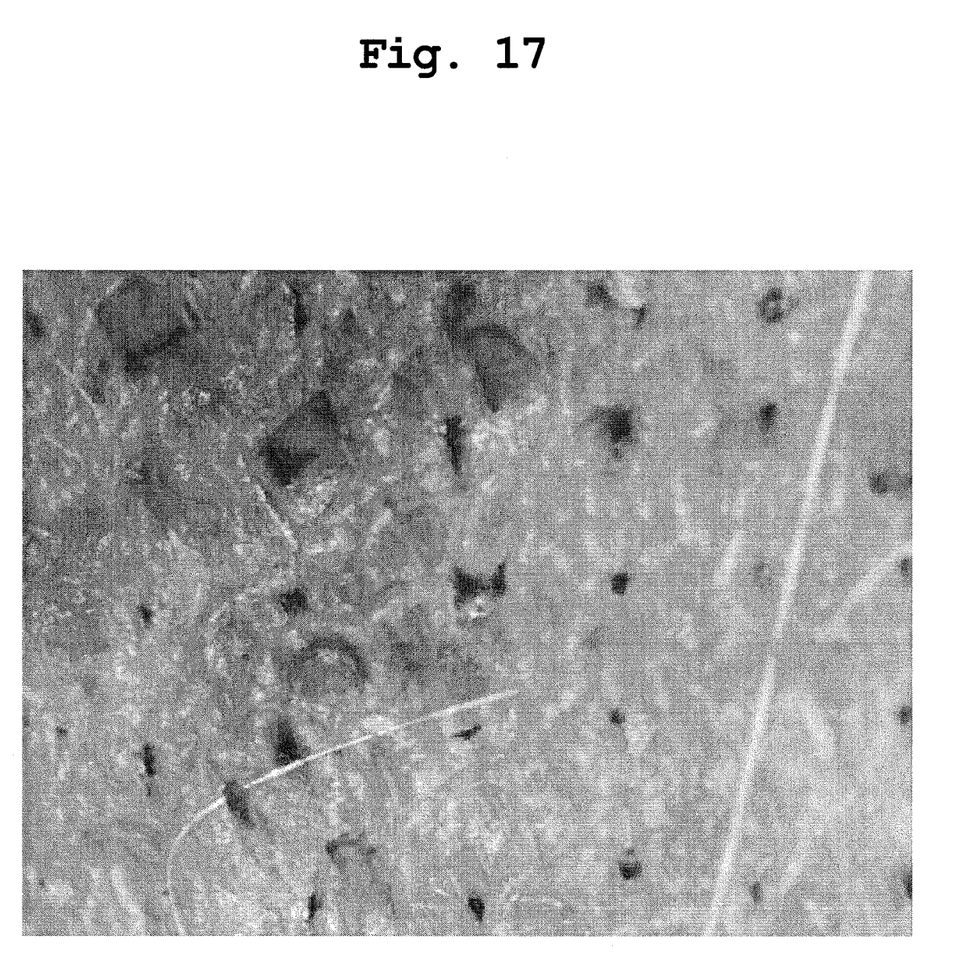
FIG. 17 shows a rat skin surface showing the result of the skin puncturing test of a rat (a skin appearance after being stained with a gentian violet solution) (magnified photograph).

As shown in FIG. 3, when the fixing member (2) is pressed with a finger, the supporting member (1) having an opening is pressed against the skin surface, and due to a counteraction against the pressure, the skin surface is elevated inside a space (concave part) fainted by the supporting member (1) and the fixing member (2). Here, the arrow in the figure indicates a direction of an applied force. The elevated skin surface starts to be punctured with the microneedle (3) placed in a central part of the concave part of the device. At this time, is since the skin surface is elevated in a direction approximately perpendicular to the fixing member (2), the small needles of the microneedle are contacted with the skin surface perpendicularly, resulting in easy penetration of the microneedle into the skin, with the tip portions of the needles being hardly broken. Thus, as shown in FIG. 17, a beautifully punctured mark is provided. In addition, in the case that an adhesive is applied onto the base surface of the microneedle and the skin surface is elevated to the base surface of the microneedle as shown in FIG. 3, when the finger force is released to remove the device composed of the supporting member (1) and the fixing member (2) from the skin surface, the fixing member (2) and the microneedle are separated from each other, and the microneedle remain on the skin surface as shown in FIG. 4. At that time, the adhesive that bonds the microneedle to the fixing member (2) is easily detachable compared to the adhesive applied onto the base surface of the microneedle. This leads to a detachment of the microneedle from the fixing member (2).

Figure 5:
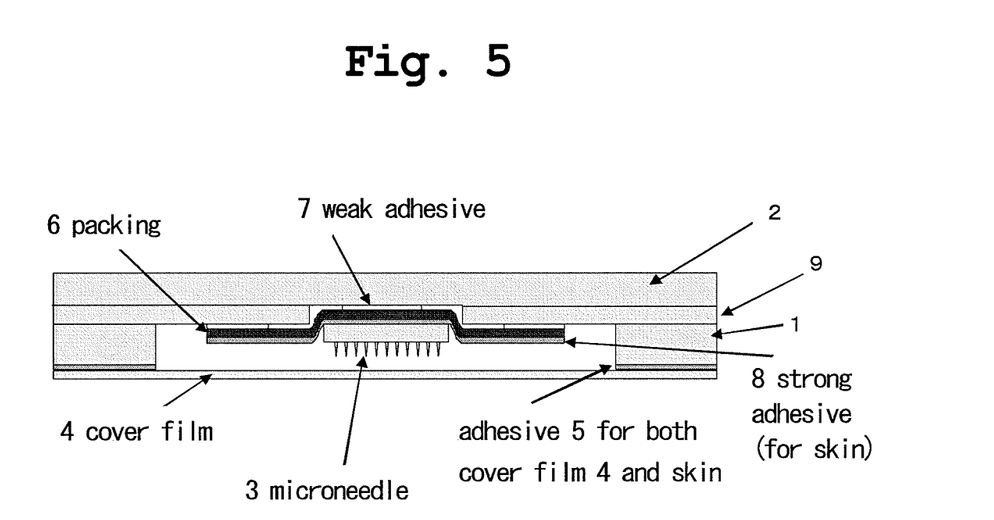
FIG. 5 is a cross-sectional view of a device of the present invention, in which a microneedle is placed on a packing, and the device has a function of puncturing skin with the microneedle and retaining the microneedle therein at the same time of plastering the packing.

Next, as shown in FIG. 5, the chip-shaped tool (device) is composed of three flat sheets. That is, a flat sheet (9) is interposed between the supporting member (1) and the fixing member (2). The flat sheet (9) has an opening in the part where the microneedle (3) is to be placed, and a packing (6) for covering the microneedle is directly adhered to the fixing member (2) with a weak adhesive (7). Then, onto the opposite surface of the packing (6), a strong adhesive (8) is applied, and thereon the microneedle (3) is placed. The packing (6) is fixed to the flat sheet (9) with a weak adhesive (7). Further, in the same manner as FIG. 1, the adhesive (5) may be applied onto the surface of the supporting member (1). The adhesive (5) is used to fix the cover film (4).

Figure 6:
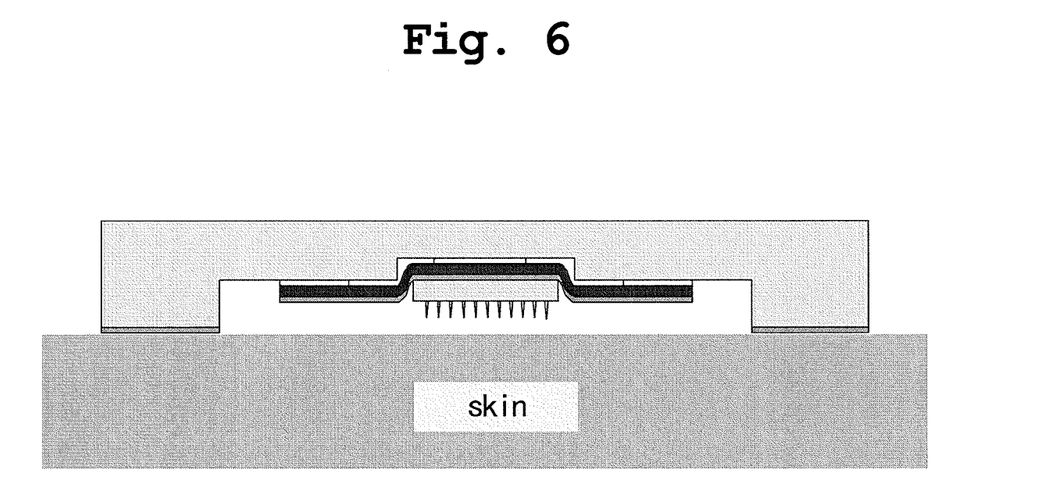
FIG. 6 is a cross-sectional view of the device of FIG. 5, in which a cover film of the device is detached therefrom and the device is placed on the skin surface.

In order to use the device of the present invention, first the cover film (4) is removed, and as shown in FIG. 6 the surface of the supporting member (1) onto which the adhesive is applied is adhered to the skin surface. At that time, the adhesive (5) also serves to fix the device to the skin surface.

Figure 7:
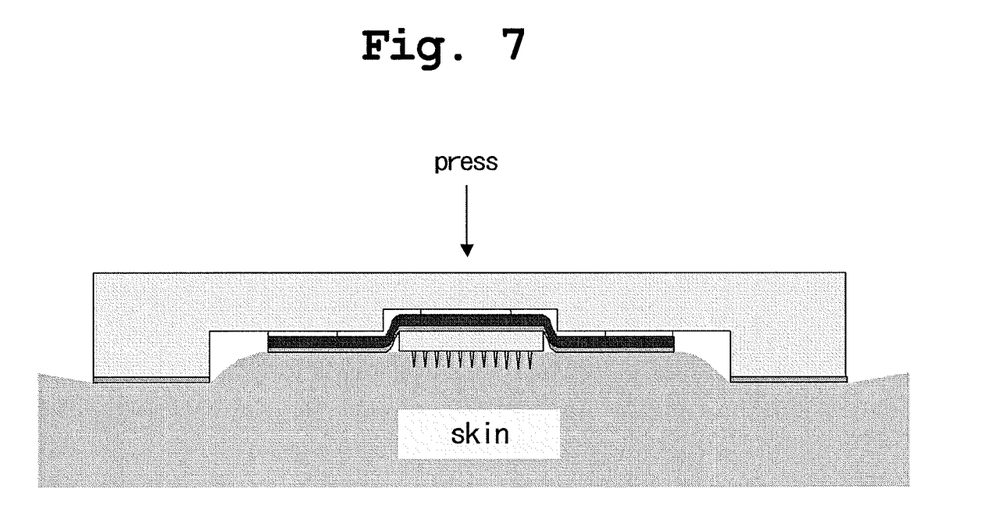
FIG. 7 is a cross-sectional view of the device of FIG. 5, showing that, when the device is pressed with a finger, the skin surface is elevated inside a concave part of the device, and the skin surface reaches an adhesive applied onto the packing and is firmly attached thereto.

As shown in FIG. 7, when the device of the present invention placed on the skin surface is pressed against the skin with a finger, the skin surface is elevated in a space defined by the fixing member (2), the flat sheet (9), and the supporting member (1). As a result, the elevated skin surface is contacted with the microneedle approximately perpendicularly and punctured with the small needles of the microneedle. As shown in FIG. 7, when the skin surface is contacted with the microneedle and the packing (6), a strong adhesive (8) applied onto the packing (6) is adhered to the skin surface.

Figure 8:
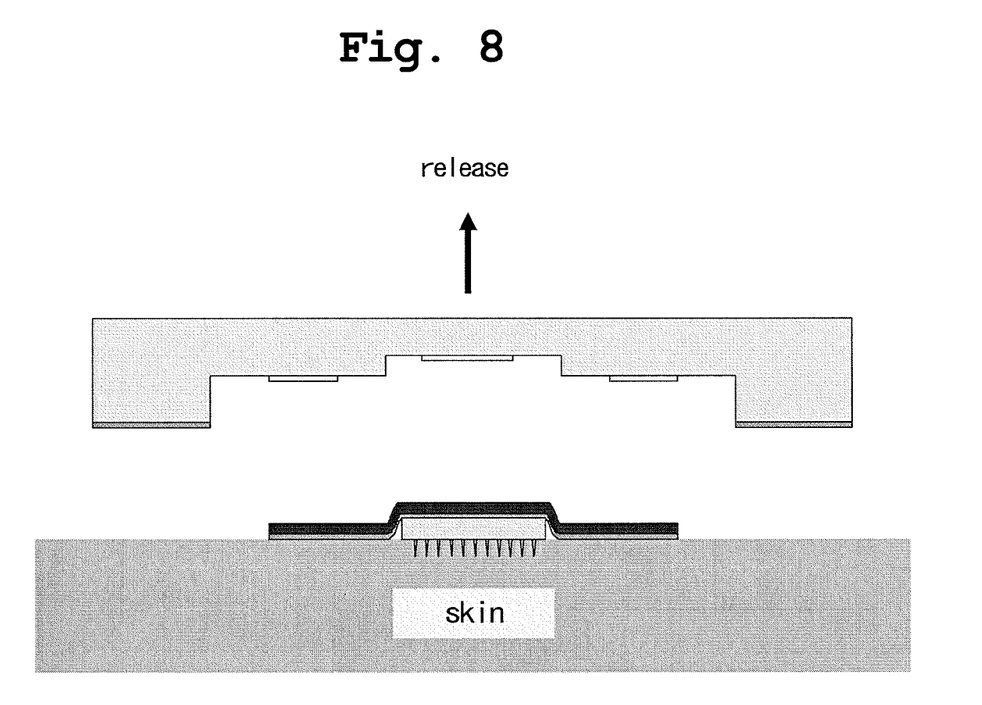
FIG. 8 is a cross-sectional view of the device of FIG. 5, showing that, when the pressure to the device is released to remove the device, the microneedle is detached from the device.

After it is confirmed that the packing (6) is adhered to the skin surface sufficiently, the finger force is released, and the device of the present invention is lifted. Then, as shown in FIG. 8, the weak adhesive (7) between the supporting member (1), the flat sheet (9), and the packing (6) is detached, and the packing (6) covering the microneedle remains on the skin surface while it is still adhered and fixed to the skin.

As such, the device of the present invention is simply pressed against the skin surface with a finger, enabling the microneedle to remain in the skin surface in an easy manner.

Figure 19:
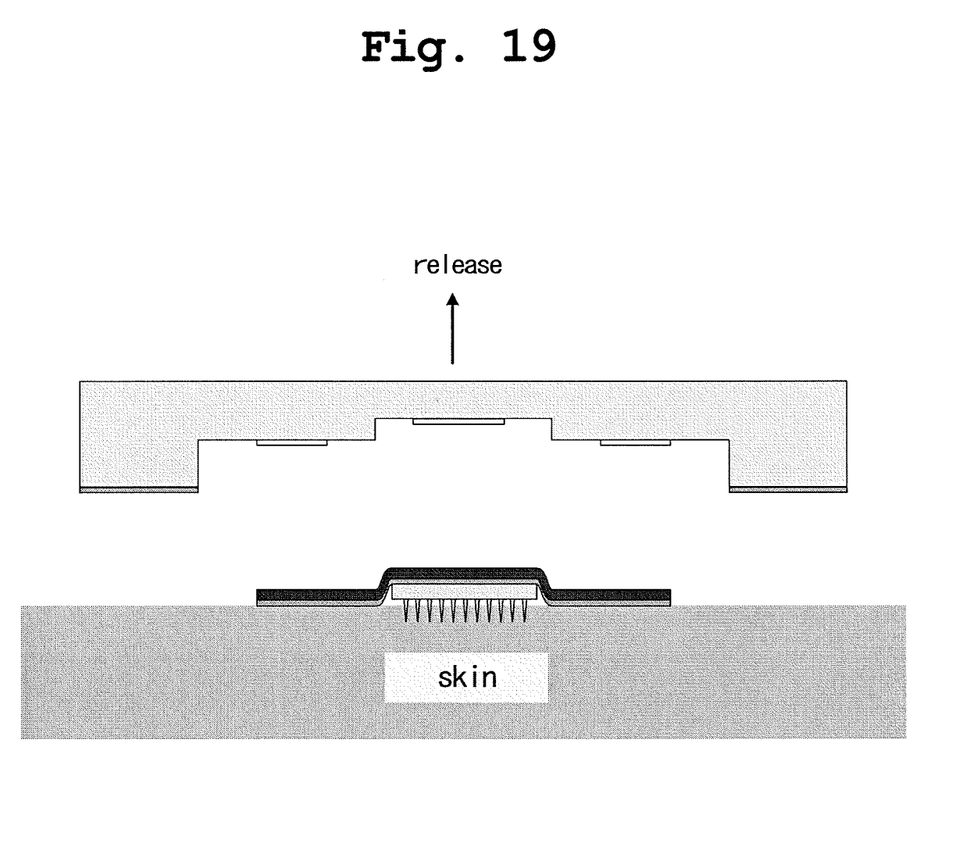
FIG. 19 shows a state in which small needles of the microneedle are inserted into the skin halfway and plastered to the skin by means of a packing member.

In FIG. 7, the microneedle is pressed against the skin surface to such deep that the skin surface reaches the base of the small needles; however, the puncturing depth of the microneedle can be selected as required. For example, since it is sufficient as long as most of the tip portion of the small needle to which a drug is applied is inserted into the skin, the skin surface is not necessarily contacted with the base part of the small needle. For example, as shown in FIG. 19, the small needle may be inserted halfway as required and plastered to the skin surface.

Figure 9:
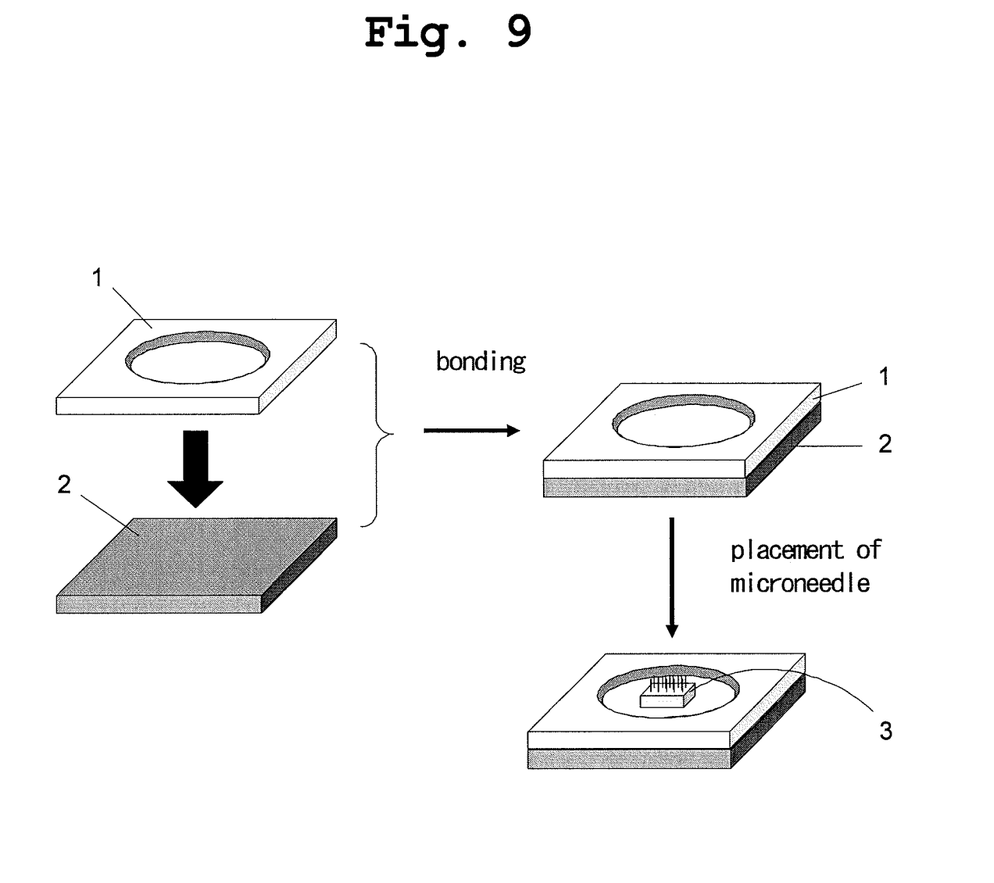
FIG. 9 shows one example of a method for producing the device of the present invention.

The device of the present invention may be produced by ordinary methods, for example, as shown in FIG. 9, by bonding the supporting member (1) having an opening for forming a concave part and the fixing member (2) constituting a bottom part of the device by melting, or by bonding them with an adhesive. The microneedle is placed in a central part of the bottom part by means of an adhesive, double-sided tape, or the like. Alternatively, the microneedle is placed on an appropriate base by means of an adhesive, double-sided tape, or the like.

The fixing member (2) constituting the bottom part is preferably a hard member so that it transmits the pressure from a finger to the skin and prevents the axis direction of the small needles of the microneedle placed on the bottom part from being shifted in linkage with the deflection of the bottom part. Examples of the hard member include those made of various materials, for example, synthetic resins, metals, wood, and the like, with at least a certain thickness. Examples of the synthetic resins include hard resins such as polyethylene, polypropylene, polyvinyl chloride, acrylic, polyethylene terephthalate, polystyrene, acrylonitrile-butadiene-styrene copolymer, polycarbonate, polyamide, fluororesin, and polybutylene terephthalate.

The supporting member (1) having an opening for forming a concave space is not particularly limited to any material, and any of resins, metals, wood, and the like may be used. Since the supporting member (1) is provided with a opening, in terms of processability, it may be preferably made of resins such as polyethylene, polypropylene, polyvinyl chloride, acrylic, polyethylene terephthalate, polystyrene, acrylonitrile-butadiene-styrene copolymer, polycarbonate, polyamide, fluororesin, and polybutylene terephthalate.

In addition, a through hole may be provided in the fixing member (2) constituting the bottom part or in the supporting member (1) having an opening, allowing air inside the device to escape therethrough, in order to enhance an elevation on skin surface inside the device.

The size of the microneedle device of the present invention is affected by the size (diameter or long side) of the base (substructure of small needles) of the microneedle to be used. For example, as shown in FIG. 1, when there is no packing, and the microneedle (3) is adhered to the fixing member (2), the size of the microneedle device is sufficient as long as it is more than that of the base of the microneedle. For example, when the microneedle is about 1 cm×1 cm, the device is required to have an inner diameter of at least 1 cm, and the outer diameter is sufficient when it is about 4 to 6 mm longer than the inner diameter. Thus, the device of the present invention is preferably at least 14 mm to 80 mm, more preferably 14 to 40 mm.

As shown in FIG. 5, when there is the packing (6), the inner diameter of the device needs to be within a range that permits the microneedle (3) to be adhered to and remain in the skin surface by means of the packing (6). Therefore, when the size (diameter or long side) of the base of the microneedle is set to be 1, the inner diameter of the device needs to be about 2.5 or more. Once the inner diameter of the device is decided, the outer diameter is sufficient when it is about 4 to 6 mm longer than the inner diameter. For example, when the base of the microneedle is 1×1 cm, the inner diameter of the device needs to be about 2.5 cm or more. Thus, the device of the present invention is preferably 29 to 80 mm, more preferably 29 to 40 mm.

In addition, as shown in FIGS. 1 and 5, one feature of the device of the present invention is that the microneedle can be protected by the cover film (4). Since there is the cover film, the small needles of the microneedle are protected against accidental contact with outside, and this makes it easy to carry the device of the present invention. After the cover film is detached from the device, the device of the present invention can be placed on the skin surface conveniently and puncture the skin with the microneedle.

When the device of the present invention is pressed against the skin, the skin is elevated to the position where the microneedle is located, and this is affected by the shape and the depth of the recessed part of the present invention. The recessed part of the present invention indicates, as shown in FIGS. 1 and 6, a concave space defined by the supporting member (1), the fixing member (2), and the like. The depth of the recessed part is designed such that the microneedle is placed in the following conditions:

a) tip portions of small needles of the microneedle are positioned inside the device such that they do not extend beyond a tip surface of the supporting member; and b) a distance between the tip portions of the small needles and the tip plane of the supporting member is "inner dimension (an average of long side and short side) of tip portion of the supporting member"×15% or shorter, preferably 12% or shorter, more preferably 8% or shorter.

Thus, the depth of the concave recessed part is sufficient as long as it is in a range where the skin surface is elevated and the tip portions of the microneedle to which a drug solution are applied are inserted into the skin. As shown in FIGS. 3 and 7, the skin surface may reach the base (substructure) of the microneedle. It is found out that preferably the microneedle in the present invention is placed in a position to satisfy the following distance, by referring to the result of Test Example 2 (Distance of Elevation on Skin), which will be described later:

a) tip portions of small needles of the microneedle are positioned inside the device such that they do not extend beyond a tip surface of the supporting member; and b) a distance between the tip portions of the small needles and the tip plane of the supporting member is "inner dimension (an average of long side and short side) of tip portion of the supporting member"×15% or shorter, preferably 12% or shorter, more preferably 8% or shorter.

On the other hand, in terms of the size of practical devices, the inner dimension (an average of long side and short side) of the tip portion of the supporting member is preferably 5 to 70 mm, more preferably 5 to 50 mm, and particularly preferably 5 to 40 mm.

The outer dimension is, assumed by the range of the practical inner dimension as described above, in a range of at least 4 to 5 mm plus the inner dimension. Accordingly, the size of the outer dimension of the device of the present invention is 10 to 80 mm, preferably 10 to 60 mm, and particularly preferably 10 to 50 mm.

The shape of the recess at the tip portion of the supporting member of the present invention is not particularly limited to, but examples thereof include a circular shape, an elliptical shape, quadrangular shapes such as square and rectangular shapes, and polygonal shapes such as pentagonal and hexagonal shapes.

The tip portions of the microneedle of the present invention are, considering the range of the practical inner diameter, positioned in a range of 0 to 10 mm from the surface of the device to be contacted with the skin, and preferably 0.4 to 8 mm, more preferably 0.4 to 6 mm.

The microneedle (3) that can be applied to the present invention may be a publicly-known microneedle made of various materials for various uses. Examples thereof include a microneedle made of silicone, such as silicone and ceramics; those made of metals, such as stainless steel, tungsten steel, nickel alloy, molybdenum, chrome, cobalt, titanium and alloy thereof; a microneedle made of biodegradable resins including aliphatic polyester resins such as polylactic acid, polyglycolic acid, a copolymer of polylactic acid and polyglycolic acid; and a microneedle made of polysaccharides such as maltose, lactose, sucrose, mannitol, and sorbitol. Among them, a microneedle made of aliphatic polyester resins, which is biodegradable materials, or those made of polysaccharides have relatively low strength and tend to be weak to impact and easily broken; however, the use of the method and the assistive tool of the present invention makes it possible to prevent or reduce the breakage of the tip needle portions of the microneedle and puncture the skin surface with the microneedle surely. Also, in the method of the present invention, it is possible to puncture the skin surface with the microneedle (3) and then easily retain the microneedle (3) in the skin, thereby enabling effective use of improved absorption or a sustained-release property of a drug by using the microneedle (3) made of a biodegradable material.

The thickness of the base (substructure) of the microneedle used in the present invention varies depending on the production method, but it is about 0.5 to 2 mm. Thus, by considering the shape and size (an average of long side and short side) of the recessed part (concave part) to be used, the position for placing the microneedle can be appropriately adjusted as explained above.

EXAMPLES

The present invention will be explained in detail with reference to Examples; however, it is not limited to any of the following Examples.

Example 1

Production of the Microneedle Device Having a Circular Concave Part

Figure 10:
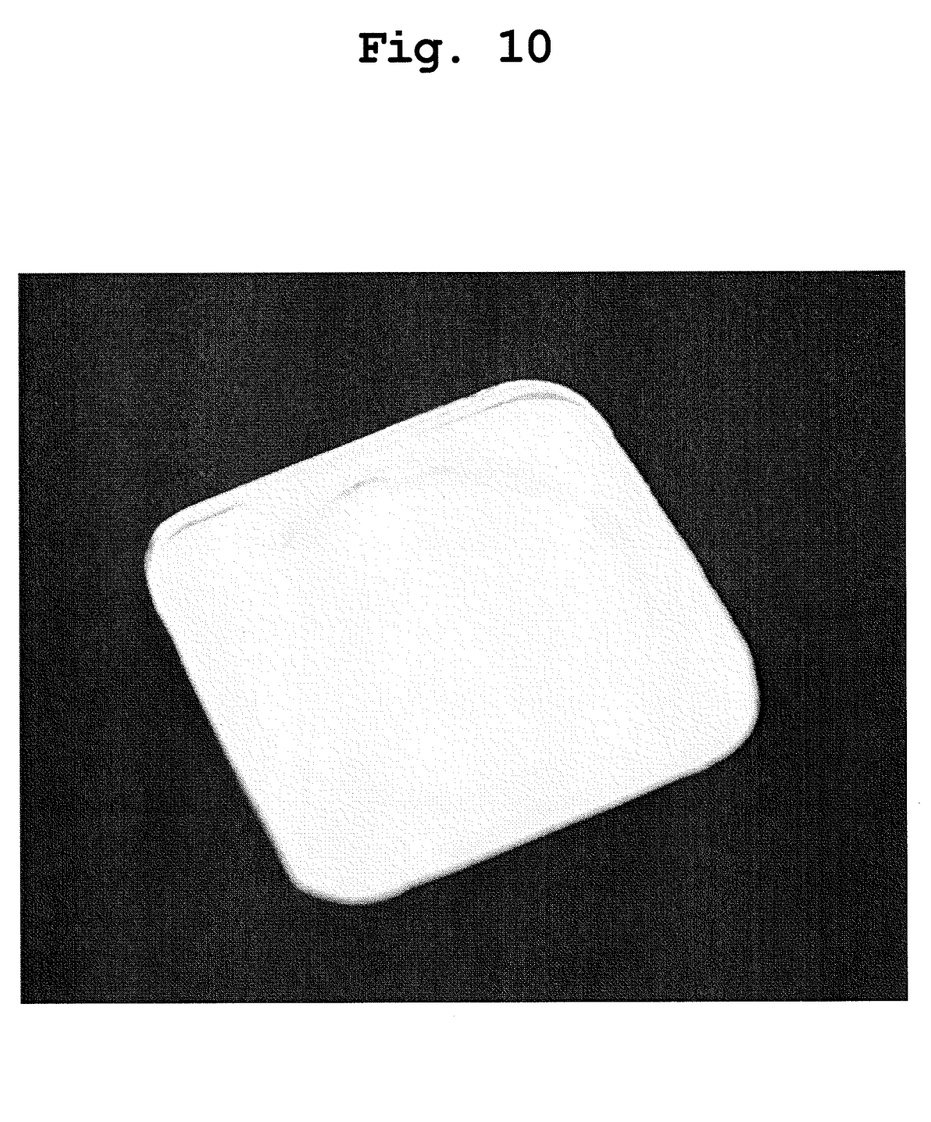
FIG. 10 shows a device of the present invention before the microneedle is placed (magnified photograph).

By using a method shown in FIG. 9, a supporting member 1 (material: polypropylene, 3×3 cm) having a thickness of 2.3 mm through which an circular opening (diameter: 2.5 mm) was formed was produced, and to this, a fixing member 2 (material: polypropylene, 3×3 cm) having a thickness of 1 mm was bonded by melting, and thus a chip having a concave part was produced as shown in FIG. 10.

Figure 11:
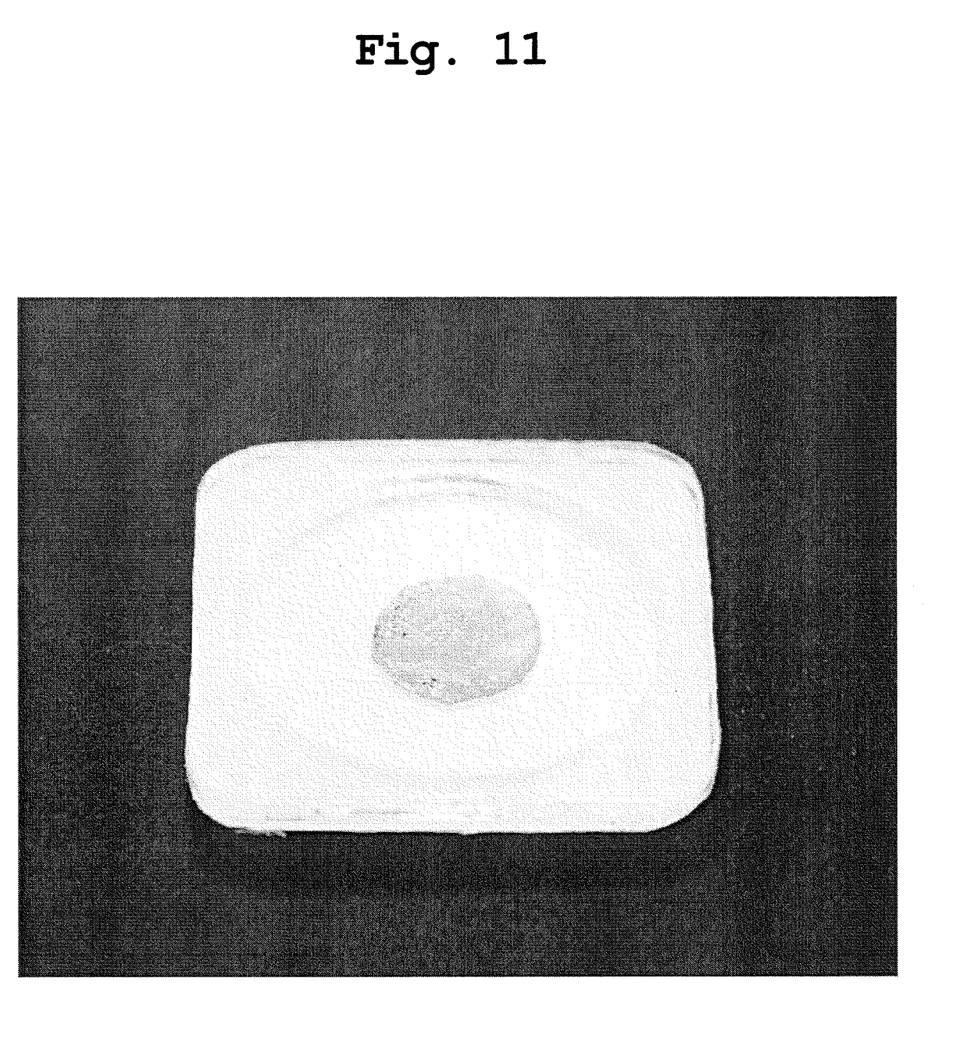
FIG. 11 shows a device of the present invention after the microneedle is placed (magnified photograph).
Figure 12:
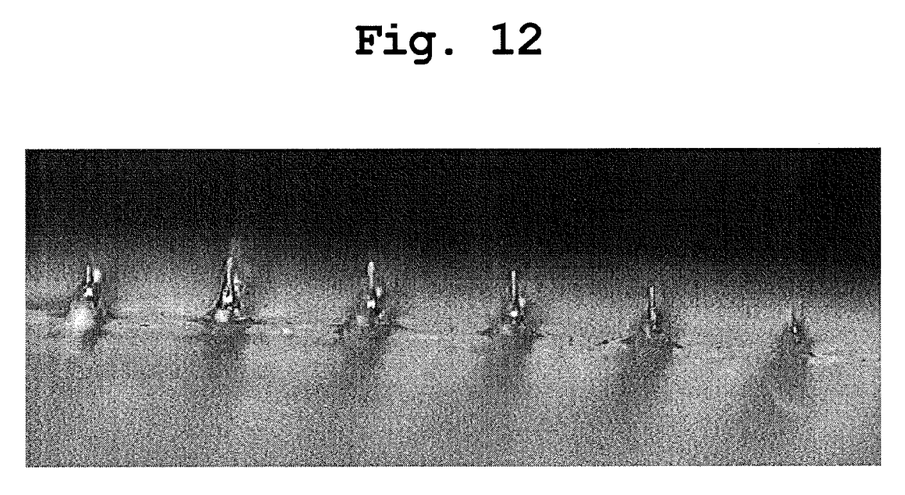
FIG. 12 shows small needle parts of the microneedle in the present invention (magnified photograph).

Next, a microneedle (1 cm×1 cm) made of PLA that was described in WO2008/093679 were fixed to a central part of the bottom part by means of an adhesive (double-sided tape, manufactured by Nichiban Co., Ltd.) to obtain a device shown in FIG. 11. As the microneedle made of PLA, a sample with a base having a thickness of 1 mm and small needles having a length of about 500 μm was used as shown in FIG. 12.

Example 2

Production of the Microneedle Device Having Various Concave Part

In accordance with Example 1, devices in which the sizes of the circular openings were changed as shown in Table 1 were produced. Further, devices in which the shapes of the openings were changed from the circular shape to square or rectangular shape as shown in Table 1 were produced. Here, the size of each fixing member constituting the bottom part was changed depending on the shape of the opening, and set to be about 5 mm longer than the length of diameter, long side, and short side. The thickness of the supporting member having the opening was 1.8 mm.

TABLE 1

| shape of opening | diameter of opening (mm) | | |
|---|---|---|---|
| circular | 5 | | |
| | 10 | | |
| | 15 | | |
| | 20 | | |
| | 25 | | |
| | 30 | | |
| | 32 | | |
| | 57 | | |
| | 72 | | |

| | long side (mm) | short side (mm) | average (mm) |
|---|---|---|---|
| square | 15 | 15 | 15 |
| | 20 | 20 | 20 |
| | 30 | 30 | 30 |
| rectangular | 20 | 15 | 17.5 |
| | 30 | 20 | 25 |
| | 30 | 15 | 22.5 |

Next, in a central part of the obtained device, the microneedle of Example 1 was placed by means of double-sided tape, to obtain a microneedle device as shown in FIG. 11.

Test Example 1

Skin Puncturing Evaluation Using the Microneedle Device

Figure 13:
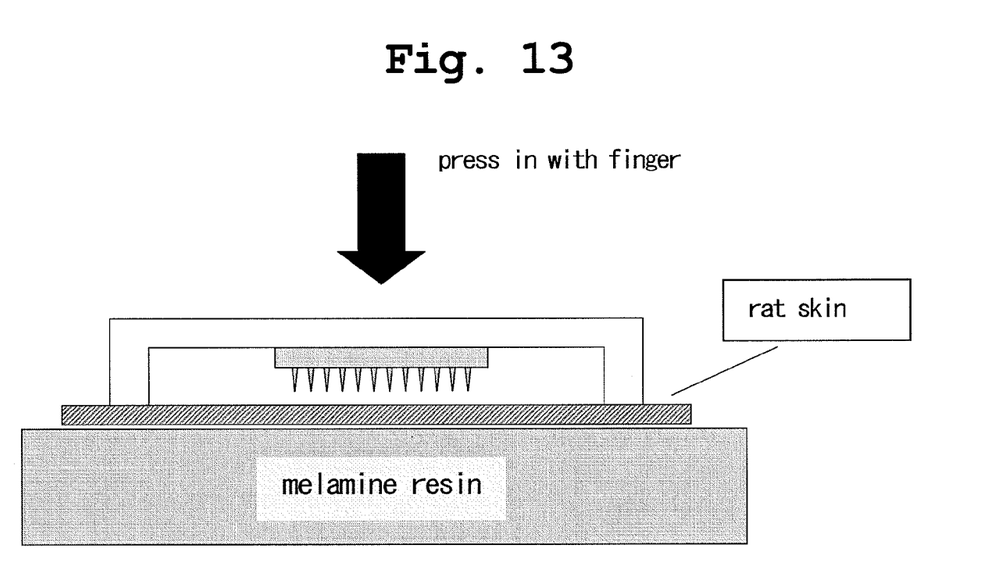
FIG. 13 is a diagram summarizing a puncturing assessment test of rat skin using a device of the present invention.

The microneedle device produced in Example 1 was used and a human skin model shown in FIG. 13 was employed to carry out a puncturing test on skin. First, on a flat plate made of melamine resin, a rat skin was placed, and thereon the microneedle device produced in Example 1 was placed. The device was pressed with a finger, and the pressure was stopped after it was confirmed that the skin had been punctured with the device. After the device and the microneedle were removed therefrom, the skin surface of the rat was stained with a gentian violet solution and observed. The punctured portions of the skin were stained with blue, making the punctured portions visible.

Figure 18:
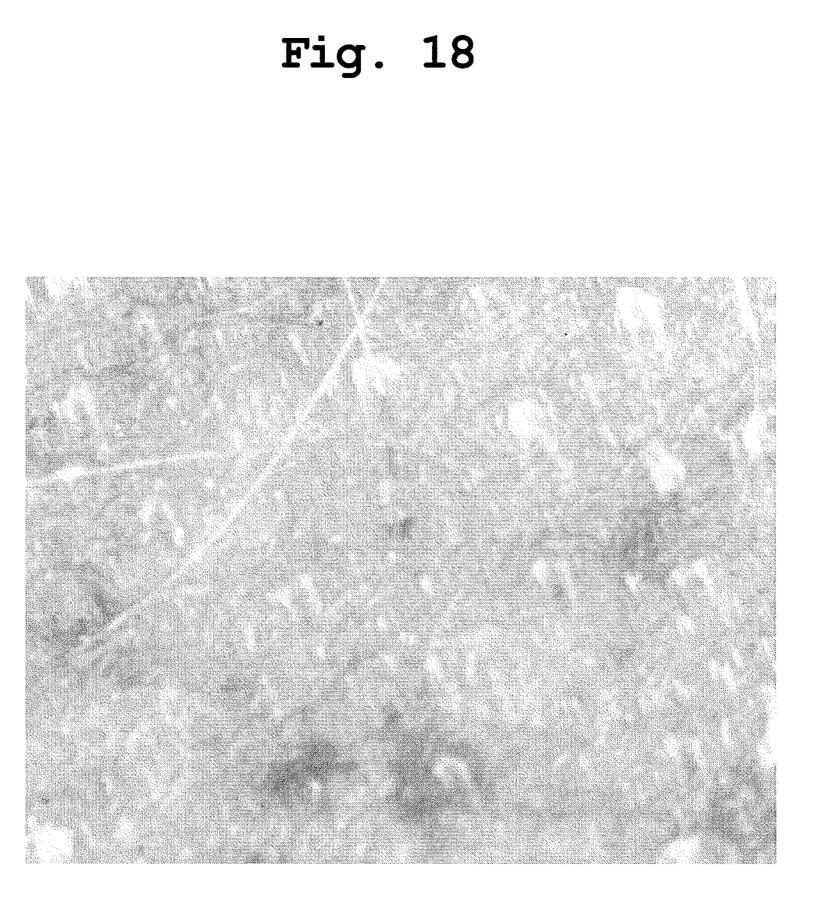
FIG. 18 shows a rat skin surface before being subjected to the skin puncturing test of a rat (magnified photograph).

The result is shown in FIG. 17. In this rat skin, the portions punctured with small needles are shown as black spots in a regular form. Here, in comparison with the rat skin before the puncture (FIG. 18), the above-mentioned matter is clearer.

Figure 14:
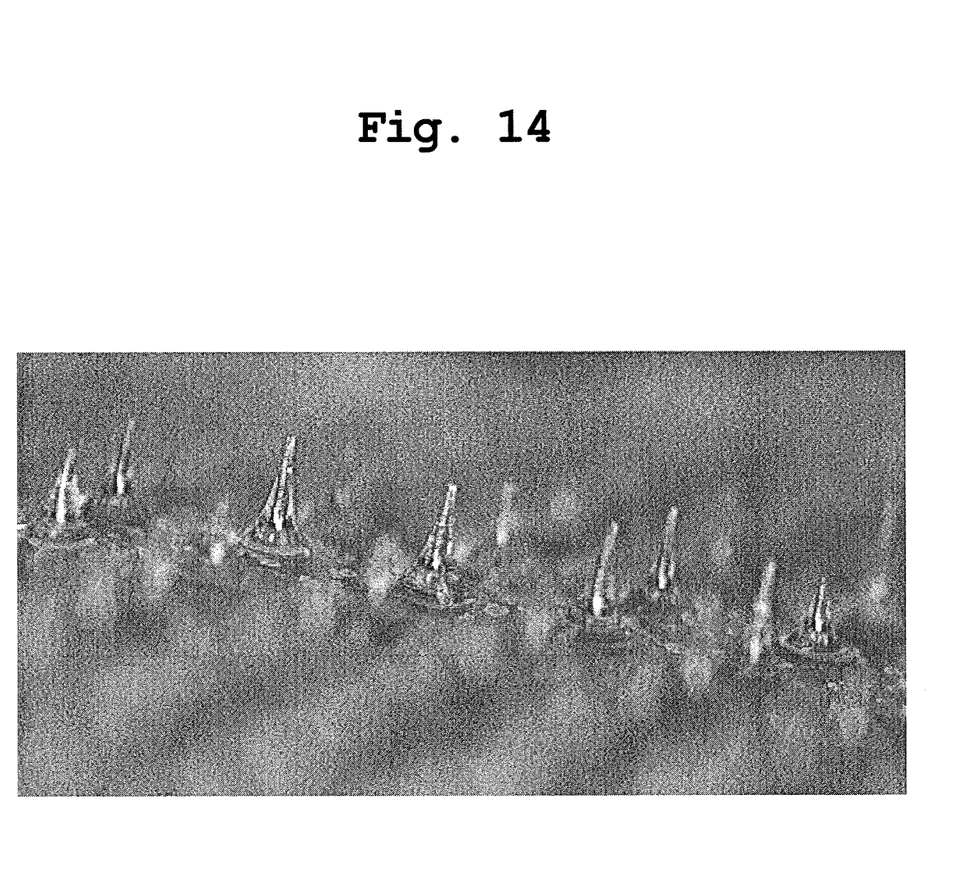
FIG. 14 shows small needle parts of the microneedle after the puncturing assessment test of rat skin (magnified photograph).

In addition, the appearance of the microneedle after the puncture was studied, and changes such as the breakage of small needles were assessed. First, a magnified photograph of the small needles of the microneedle before puncturing the rat skin shown in FIG. 12 was compared with a magnified photograph of the small needles of the microneedle after puncturing the rat skin shown in FIG. 14. Then, it was found out that there was no significant change in the shape of the small needles, and the microneedle punctured the skin appropriately with no breakage or bending in a lateral direction.

The above results clearly show that the microneedle device of the present invention can achieve the desired purpose.

Test Example 2

Evaluation of Distance of Elevation on Skin on Press-Adhering the Microneedle Device A device produced in Example 2 at the point before a microneedle was placed was used and press-adhered to the skin, and how much an elevation on skin appeared was measured and assessed. Here, the thickness of the supporting member (1) was adjusted in accordance with the distance of the elevation on skin.

As the assessment method, in the same manner as in Test Example 1, on a flat plate made of melamine resin, a rat skin was placed, and thereon the device produced in Example 2 was placed. The device was pressed with a finger force, and how much rat skin was elevated was evaluated. The results are shown in Table 2 collectively.

TABLE 2

| shape of opening | diameter of opening (mm) | | distance of elevation on skin on press-adhering (mm) | ratio based on diameter |
|---|---|---|---|---|
| circular | 5 | | 0.4 | 8% |
| | 10 | | 0.8 | 8% |
| | 15 | | 1.5 | 10% |
| | 20 | | 2.2 | 11% |
| | 25 | | 3 | 12% |
| | 30 | | 3.8 | 13% |
| | 32 | | 4.5 | 14% |
| | 57 | | 7 | 12% |
| | 72 | | 8.8 | 12% |

| | long side (mm) | short side (mm) | average (mm) | | |
|---|---|---|---|---|---|
| square | 15 | 15 | 15 | 1.5 | 10% |
| | 20 | 20 | 20 | 2.2 | 11% |
| | 30 | 30 | 30 | 3.8 | 13% |
| rectangular | 20 | 15 | 17.5 | 2.2 | 13% |
| | 30 | 20 | 25 | 3 | 12% |
| | 30 | 15 | 22.5 | 3 | 13% |

Figure 15:
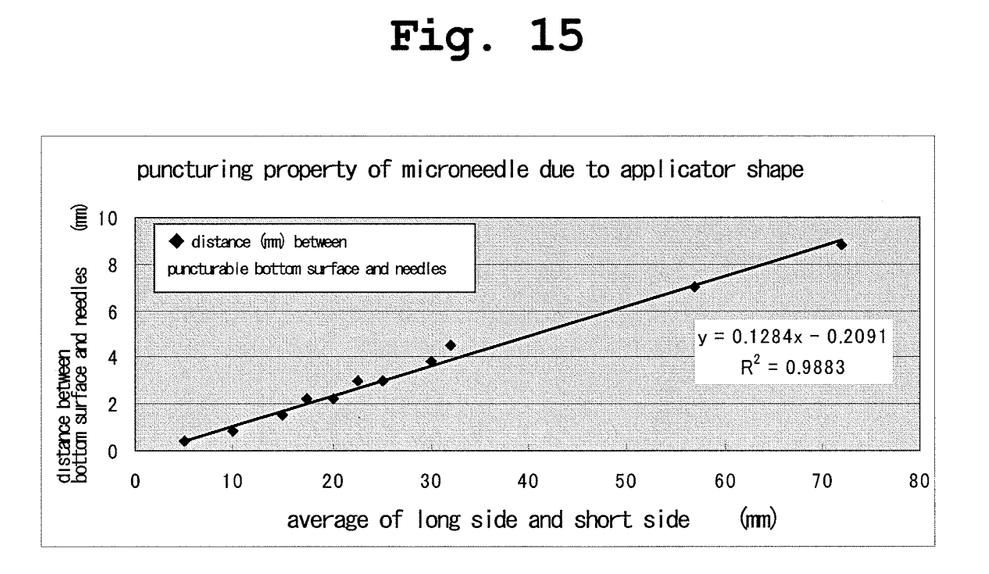
FIG. 15 shows a correlation between the shape of a concave part of the device and the distance of an elevation on the skin surface.
Figure 16:
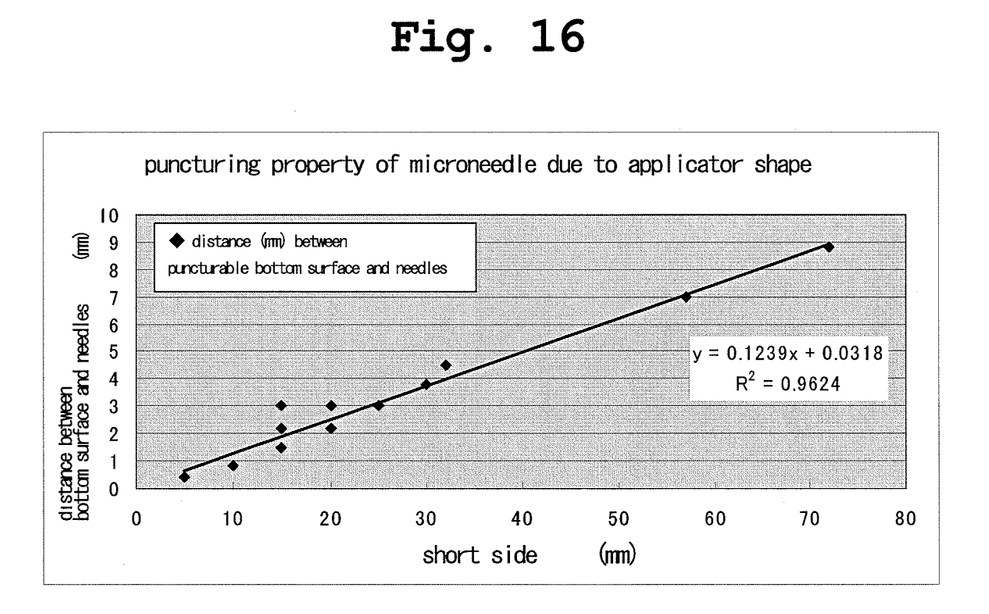
FIG. 16 shows a correlation between the shape of a concave part of the device and the distance of an elevation on the skin surface.

By using the results shown in Table 2, graphs were made in terms of the relationship between the diameter, short side or long side of the opening and the distance of the elevation on the skin. Then, the graphs showed positive correlations as shown in FIGS. 15 and 16. That is, it was shown that the longer the diameter of the opening was, the longer the distance of the elevation on skin became, and the degree of the distance of the elevation on skin was highly correlated with the diameter or an average value of the short side and the long side.

From the result, an appropriate thickness of the flat sheet having the opening can be calculated. That is, by considering the thickness of the base of the microneedle and the height of the microneedle placed thereon, it is possible to calculate an appropriate thickness of the flat sheet in order to puncture the skin. It is clear that, when the thickness of the flat sheet having the opening is 2.3 mm as in Example 1, with the opening of a circular shape, at least 15 mm in diameter is necessary for the opening, otherwise the skin is not elevated so much as to permit the small needles to puncture the skin.

INDUSTRIAL APPLICABILITY

The device of the present invention is a microneedle device which is easily portable and allows for easy puncturing, so that it can be easily dealt with by ordinary people. Accordingly, the device can be applied to wide uses such as self-injection of insulin etc., and vaccine injection at the time of a pandemic. In addition, the device hardly causes breakage of small needles of the microneedle, and ensures the injection of drugs at the time of puncturing. As a result, a microneedle patch, which is easily portable and ensures convenient drug administration to the skin, can be produced.

DESCRIPTION OF REFERENCE SIGNS

1: Supporting member for forming a recessed part (concave part)
2: Fixing member for forming a bottom part
3: Microneedle
4: Cover film
5: Adhesive for both cover film and skin
6: Packing
7: Weak adhesive
8: Strong adhesive
9: Flat sheet ensuring space for housing packing

The invention claimed is:

1. A microneedle device comprising:
a concave part,
a flat plate fixing member for fixing a microneedle, and
a supporting member at or near a periphery of the flat plate fixing member,
wherein
the supporting member has an opening for forming the concave part,
the flat plate fixing member constitutes a bottom part of the microneedle device and is a hard member configured to transmit pressure from a finger to skin to thereby elevate the skin surface inside the concave part and to prevent the axial direction of small needles of the microneedle from being shifted,
the supporting member comprises a resin, and
the microneedle is placed in a central part of the concave part such that:
(a) tip portions of small needles of the microneedle are positioned inside the microneedle device from a tip surface of the supporting member, and
(b) a distance between the tip portions of the small needles and the tip surface plane of the supporting member is 15% or shorter than the inner dimension of the opening.

2. The microneedle device according to claim 1, wherein the inner dimension of the opening of the supporting member is 5 to 70 mm.

3. The microneedle device according to claim 2, wherein the inner dimension of the opening of the supporting member is 5 to 50 mm.

4. The microneedle device according to claim 3, wherein the shape of the opening of the supporting member is a circular shape.

5. The microneedle device according to claim 4, wherein the circular shape has a diameter of 5 to 32 mm.

6. The microneedle device according to claim 3, wherein the shape of the opening of the supporting member is an elliptical shape.

7. The microneedle device according to claim 3, wherein the shape of the opening of the supporting member is a polygonal shape.

8. The microneedle device according to claim 7, wherein the polygonal shape is a square shape.

9. The microneedle device according to claim 1, wherein the shape of the opening of the supporting member is a circular shape, an elliptical shape, or a polygonal shape.

10. The microneedle device according to claim 9, wherein the polygonal shape is a square shape.

11. The microneedle device according to claim 9, wherein the circular shape has a diameter of 5 to 32 mm.

12. The microneedle device according to claim 1, wherein the shape of the opening of the supporting member is a rectangular shape, and the inner dimension is an average of a long side and a short side of the rectangular shape.

13. The microneedle device according to claim 1, wherein the flat plate fixing member comprises a synthetic resin selected from polyethylene, polypropylene, polyvinyl chloride, acrylic, polyethylene terephthalate, polystyrene, acrylonitrile-butadiene-styrene copolymer, polycarbonate, polyamide, fluororesin, and polybutylene-terephthalate.

14. The microneedle device according to claim 1, wherein the resin of the supporting member is selected from polyethylene, polypropylene, polyvinyl chloride, acrylic, polyethylene terephthalate, polystyrene, acrylonitrile-butadiene-styrene copolymer, polycarbonate, polyamide, fluororesin, and polybutylene-terephthalate.

15. The microneedle device according to claim 1, wherein the flat plate fixing member and the supporting member comprise polypropylene.

* * * * *